US007074759B2

(12) United States Patent
Naidu

(10) Patent No.: US 7,074,759 B2
(45) Date of Patent: *Jul. 11, 2006

(54) TREATMENT OF CASE-READY FOOD PRODUCTS WITH IMMOBILIZED LACTOFERRIN (IM-LF) AND THE PRODUCTS SO PRODUCED

(76) Inventor: A. Satyanarayan Naidu, 22810 Mountain Laurel Way, Diamond Bar, CA (US) 91765

( * ) Notice: Subject to any disclaimer, the term of this patent is extended or adjusted under 35 U.S.C. 154(b) by 0 days.

This patent is subject to a terminal disclaimer.

(21) Appl. No.: 10/602,118

(22) Filed: Jun. 23, 2003

(65) Prior Publication Data

US 2004/0043922 A1 Mar. 4, 2004

Related U.S. Application Data

(63) Continuation-in-part of application No. 09/980,062, filed on May 10, 2002, which is a continuation-in-part of application No. 09/322,700, filed on May 28, 1999, now Pat. No. 6,172,040.

(51) Int. Cl.
*A23B 4/20* (2006.01)
*A23L 1/314* (2006.01)
*A61K 38/02* (2006.01)

(52) U.S. Cl. .......................... 514/6; 426/310; 426/332; 426/335; 426/532

(58) Field of Classification Search .................. 422/28, 422/32; 424/439, 442; 426/302, 310, 321, 426/322, 326, 332, 335, 532, 574, 652; 514/6, 514/8, 21; 530/395, 400, 810, 811, 812, 530/813, 814, 815, 816, 817
See application file for complete search history.

(56) References Cited

U.S. PATENT DOCUMENTS

| | | | | |
|---|---|---|---|---|
| 4,791,193 | A * | 12/1988 | Okonogi et al. | 530/416 |
| 5,106,643 | A * | 4/1992 | Laufer | 426/565 |
| 5,597,597 | A * | 1/1997 | Newman | 426/248 |
| 6,066,348 | A * | 5/2000 | Yuan et al. | 426/236 |
| 6,172,040 | B1 * | 1/2001 | Naidu | 514/6 |
| 6,291,003 | B1 * | 9/2001 | Riemann et al. | 426/511 |
| 2003/0229011 | A1 * | 12/2003 | Braun et al. | 514/6 |

FOREIGN PATENT DOCUMENTS

WO WO 00/72690 A1 * 12/2000
WO WO 00/72874 A1 * 12/2000

OTHER PUBLICATIONS

Harper et al. Dairy Technology and Engineering. Westport: The AVI Publ. Co., Inc. pp. 20-23, 28-37. 1976.*
Naidu et al. Milk Lactoferrin—Natural Microbial Blocking Agent (MBA) For Food Safety. Environmental & Nutritional Interactions. 1998, vol. 2, pp. 35-50.*

* cited by examiner

*Primary Examiner*—Jeffrey Edwin Russel
(74) *Attorney, Agent, or Firm*—Jeffrey F. Craft; Jackson, DeMarco, Tidus & Peckenpaugh; Paul D. Chancellor

(57) ABSTRACT

Disclosed is a method for reducing the microbial contamination in products, such as case-ready meat products, including ready-to-eat meat products, subject to microbial contamination, including contamination by *E. coli* and *Listeria monocytogenes*. The food products are treated with a defined dispersion of lactoferrin immobilized on a naturally occurring substrate via the N-terminus region of the lactoferrin. Also disclosed are case-ready food products, including ready-to-eat food products, prepared in accordance with such a method.

4 Claims, No Drawings

TREATMENT OF CASE-READY FOOD PRODUCTS WITH IMMOBILIZED LACTOFERRIN (IM-LF) AND THE PRODUCTS SO PRODUCED

CROSS-REFERENCE TO RELATED APPLICATIONS

The within invention is a continuation-in-part of U.S. Ser. No. 09/980,062 filed May 10, 2002 which is a continuation-in-part of U.S. Ser. No. 09/322,700, filed May 28, 1999, now U.S. Pat. No. 6,172,040, which are hereby incorporated by this reference.

Throughout this application various publications are referenced within parentheses. The disclosures of these publications in their entireties are hereby incorporated by reference in this application in order to more fully describe the state of the art to which this invention pertains.

BACKGROUND OF THE INVENTION

1. Field of the Invention

This invention relates to the chemical arts. In particular, it relates to antimicrobial agents and their use.

2. Discussion of the Related Art

Edible tissues of a healthy meat animal are essentially sterile prior to slaughter. Various innate host defense mechanisms at the external and internal organ surfaces create an effective barrier and prevent microorganisms from invading the tissues of a live animal. As soon as the animal is slaughtered, however, the natural defenses against invading microbes virtually disappear, and the exposed tissues become highly susceptible to microbial colonization and proliferation. Meat of the freshly slaughtered animal is prone to contamination with a variety of bacterial species, influenced by the degree of sanitation practiced during the meat processing and packing operations.

The economic impact of food-borne pathogenic outbreaks and the shorter than desired shelf life of refrigerated products, even vacuum packaged refrigerated products, has necessitated the search for an effective antimicrobial system for the meat industry. Various methods are currently in practice to control *Escherichia coli* (*E. coli*), *Listeria monocytogenes*, and other microbial contamination in foods, but, unfortunately, they suffer from a variety of drawbacks.

For example, in the meat industry, acid washing of beef carcasses is currently being employed as a microbial intervention. However, recent studies have shown that certain types of *E. coli*, such as the verotoxic strains of serotype O157:H7 and vancomycin-resistant strains of *Enterococcus faecium*, can survive acid conditions, while at the same time produce harmful toxins. The meat industry is also irradiating meat in an attempt to control pathogens and food spoilage organisms. However, studies have shown that although irradiation appears to be effective at killing some types of *E. coli*, there are still various other microorganisms, including strains of *Brochothrix thermospacta* and *Bacillus pumilus*, known to be radiation resistant and thus are able to survive such processes. Irradiation also can produce undesirable changes in the texture and/or organoleptic quality of beef. Further, both of these methods are cidal processes that kill microorganisms leaving endotoxins, microbial debris and other proinflammatory substances which can cause undesirable immunological reactions in the host. Finally, neither of these methods excludes the possibility of post-processing contamination once the beef is treated for microbial contaminants.

In addition to food-borne pathogens, microbial spoilage of packaged foods, including fresh meats, is a significant concern to the food industry. Under certain conditions, it is possible to control microbes, including enteric pathogens, using such well known antimicrobial agents as acids, salts, oxidative agents, antibiotics, bacteriocins, and the like. Typically, the mode of action of these agents is “cidal”—the direct killing of the microbes, or “stasis”—the inhibition of microbial growth/multiplication. Another mode of action for conventional antimicrobial agents is opsonization. The agents intervene by promoting microbial phagocytes by macrophages.

Certain cellular research relating to the mechanisms of microbial biosurface interactions has led to the identification of another mode of action, microbial blocking, and a new class of antimicrobial agents, microbial blocking agents (MBAs). MBAs are naturally occurring biological substances that block microbial adhesion-colonization, retard growth-multiplication, and neutralize the adverse effects of proinflammatory cell debris.

It has not proved possible to apply such microbial blocking agents during meat packing or other food processing conditions, because of the difficulty of delivering a biofunctionally active and structurally stable MBA to the food product to be treated. The difficulty is compounded when the food product is a meat product, because a controlled milieu is required for a broad-spectrum activity of MBA to block various microorganisms on a chemically complex and heterogenous meat tissue.

Lactoferrin (LF) is an iron-binding glycoprotein present in milk and various mammalian secretions (e.g, saliva, tears, mucus, and seminal fluids). Crystallographic studies of LF indicate a bilobate structure (N-terminus and C-terminus lobes) with one iron-binding site in each lobe. LF has ability to reversibly bind two $Fe^{3+}$ ions per lobe in coordination with two $CO_3^{2-}$ ions. LF can release the bound iron in a fully reversible manner, either on exposure to lowered pH (below 4.0) or on receptor binding. This high affinity for iron is linked to many of its biological functions including antimicrobial effects. Various laboratory studies have reported that the structural integrity of LF is critical for its antimicrobial effects against bacteria, fungi, protozoa, and viruses.

However, the activity of LF, like the activity of most proteins, is highly dependent on the three-dimensional or tertiary structure of the protein. If the protein does not have the proper conformation its activity is diminished or lost. LF’s instability limits it usefulness. Milieu conditions such as metals (iron in particular), carbonic ions, salts, pH and conductivity affect the antimicrobial properties of LF. In addition, protein isolation procedures, storage, freezing-thawing, can adversely affect the biofunctionality of LF. Consequently, before LF can be used for commercial application, it would be expected to become denatured or inactivated, and lose its antimicrobial properties.

In fact, under certain conditions, when the LF molecule is degraded or denatured, cationic peptide fragments are generated. These cationic peptide fragments exhibit a nonspecific antimicrobial activity, making them absolutely unsuitable as an ingredient in a food product. The consumer of a food product does not want to ingest a non-specific antimicrobial agent, because of the agent’s adverse affect on the desirable microbes always present in a human body, particularly within the gastrointestinal tract.

Thus, an antimicrobial agent is needed for blocking microbial contamination in foods, meats, in particular, that does not pose the undesired affects of cidal antimicrobial systems but that also exhibits carry through properties for the prevention of post-processing contamination.

SUMMARY OF THE INVENTION

The present invention relates to a method for treating products with a sufficient amount of lactoferrin to reduce microbial contamination and the immobilized lactoferrin used in the process. More particularly, the present invention relates to immobilized lactoferrin and mixtures of immobilized lactoferrin and native lactoferrin having increased antimicrobial activity against a wide variety of bacteria and other food spoilage as well as increased stability for use in various stages of food processing, and a method for treating foods, particularly case-ready food products, including ready-to-eat foul products. The method is of use in preventing microbial contamination by a wide variety of microbes including enterotoxigenic *Escherichia coli*, enteropathogenic *Escherichia coli, Listeria monocytogenes, Shigella dysenteriae, Shigella flexneri, Salmonella typhimurium, Salmonella abony, Salmonella dublin, Salmonella hartford, Salmonella kentucky, Salmonella panama, Salmonella pullorum, Salmonella restock, Salmonella thompson, Salmonella virschow, Campylobacter jejuni, Aeromonas hydrophila, Staphylococcus aureus, Staphylococcus hyicus, Staphylococcus epidermidis, Staphylococcus hominis, Staphylococcus warneri, Staphylococcus xylosus, Staphylococcus chromogenes, Bacillus cereus, Bacillus subtilis, Candida albicans*, and such radiation-resistant bacteria as: *Brochothrix thermospacta, Bacillus pumilus, Enterococcus faecium, Deinococcus radiopugnans, Deinococcus radiodurans, Deinobacter grandis, Acinetobacter radioresistens, Methylobacterium radiotolerans*. It is of particular use in preventing microbial contamination by verotoxic *Escherichia coli*, including serotype O157:H7, and *Listeria monocytogenes*.

The lactoferrin is immobilized on a naturally occurring substrate via the N-terminus region of the lactoferrin. Suitable substrates include proteins, polysaccharides, cellulose, nucleic acids, nucleotides, and lipids. Preferred substrates include collagen, gelatin, pectin, fibronectin, casein, mucin, heparan-sulfate, carrageenan, deoxyribonucleic acid, adenosine triphosphate or a triglyceride, pectin galactose-rich polysaccharide being most preferred.

In some embodiments, the lactoferrin is applied as an aqueous solution containing a mixture of the immobilized lactoferrin and native lactoferrin, where the concentration of the mixture in the solution is from about 0.001 to about 2.5% wt/vol and the ratio of immobilized lactoferrin to native lactoferrin in the mixture is from about 1:1 to about 1:10, preferably about 1:1 to 1:5, and most preferably about 1:1. And in some embodiments, the mixture contains about 1% wt/vol immobilized lactoferrin and about 1% wt/vol native lactoferrin.

In some embodiments, the aqueous solution further includes a buffer system that contains a physiologically acceptable acid, such as oxalic acid, ethylenediamine tetraacetic acid, and citric acid, preferably ethylenediamine tetraacetic acid and citric acid, a physiologically acceptable base, preferably sodium bicarbonate, and a physiologically acceptable salt, such as calcium chloride, potassium chloride and sodium chloride, preferably sodium chloride. The molar ranges of acid:base:salt is generally about 0.1 to 0.0001M (acid): 1 to 0.001M (base): 10 to 0.01M (salt); with 0.01–0.001M (acid): 0.1 to 0.01M (base): 1 to 0.01M (salt), preferred; and 0.001M (acid): 0.01M (base): 0.1M (salt), most preferred. Typically, the concentration of lactoferrin on the surface of a composition treated in accordance with the inventive method is from about 0.0001 to about 10 mg/sq. inch.

These and other advantages and features of the present invention will be described more fully in a detailed description of the preferred embodiments which follows.

DETAILED DESCRIPTION OF THE PREFERRED EMBODIMENTS

The inventive methods involve treating case-ready food products and particularly ready-to-eat food products, with lactoferrin (LF) immobilized on a naturally occurring substrate via the amino terminus (N-terminus) region of the lactoferrin molecule. The LF and immobilized lactoferrin (Im-LF) useful in accordance with the inventive methods include or contain glycosylated or unglycosylated LF peptides. The terms “LF”, “LF protein”, and “LF peptide” are used interchangeably herein. A full length LF peptide sequence has about 600 to about 800 contiguous amino acids. For example, native human LF is about 703 amino acids long; native bovine LF is about 651 amino acids long. Other useful mammalian LF sequences are of various but similar lengths. Useful LF peptides include full length native LF peptides and also include LF peptides lacking one to about eleven contiguous amino acids from the extreme end of the N-terminus region or the extreme end of the C-terminus region of a native LF peptide amino acid sequence. Also useful are LF peptides having sequences variant in one or more amino acid residues compared to a native LF sequence, but that remain at least partially functional. The term “functional”, when used herein as a modifier of LF protein(s) or peptide(s), refers to a polypeptide that exhibits both the ability to bind at its N-terminus to a substrate, i.e., become immobilized, and also the antimicrobial activity attributed to native LF amino acid sequences. Thus, the term “native LF”, in reference to mixtures of native LF and Im-LF, encompasses functional LF having a variant amino acid sequence.

The LF peptide can be isolated from mammalian sources (humans, cows, sows, mares, transgenic animals and the like), biological secretions such as colostrum, transitional milk, matured milk, milk in later lactation, and the like, or processed products thereof such as skim milk and whey. Also useful for the isolation of LF is well known recombinant DNA technology, whereby cloned LF-encoding genes are expressed in procaryotic and/or eucaryotic cells. The LF peptide is isolated by any conventional method, such as by chromatography, ion-exchanger, molecular-sieve or affinity column. Suitable LF also is commercially available from DMV International Nutritionals, the Netherlands; Morinaga Milk Company, Japan; BioPole, Belgium; and Avonmore-Waterford, USA.

The LF can be, but is not necessarily, of homologous origin with respect to the composition, product, or surface that is treated, or with respect to the vertebrate subject to which it is administered, in accordance with the present methods. Lactoferrins of heterologous mammalian origin with respect to the surface are also useful. Thus, for example, in accordance with the inventive method, an Im-LF of human origin functions to reduce or inhibit microbial contamination of meat or flesh of non-human origin, or functions to inhibit microbial growth in or on human and/or non-human vertebrates. Similarly, bovine Im-LF can be used to treat either bovine or non-bovine meat or meat products and is useful in cosmetics, cleansers, food supplements, or medicaments intended for human use or for bovine and/or non-bovine veterinary uses. However, for systemic delivery to human or non-human vertebrates, in vivo, homologous LF is preferred to avoid adverse immunoreactions.

The LF is immobilized on a naturally occurring substrate via the N-terminus region of the lactoferrin. Suitable substrates include proteins, polysaccharides, cellulose, nucleic acids, nucleotides, and lipids. Preferred substrates include collagen, gelatin, fibronectin, casein, mucin, heparan-sulfate, carrageenan, deoxyribonucleic acid, adenosine triphosphate or a triglyceride.

Other suitable biologically active substrates include proteins, such as collagen, denatured collagen (gelatin), pectin, fibronectin, and casein; polysaccharides, such as mucin, heparan-sulfates, carrageenan, and cellulose; nucleic acids and their nucleotides, such as deoxyribonucleic acid and adenosine triphosphate; and lipids such as triglycerides.

The LF is immobilized on the substrate using any suitable technique. For example, LF can be immobilized simply by mixing the LF with the biologically active substrate in a suitable medium, such as deionized water. The immobilization process is dependent on the quality of the substrate as well as the quality of the LF. For example, in most of the commercially available lactoferrins, there is variation in the level of impurities (range: 4–10%), degree of non-specific cidal activity (range: 20–40%), and extent of protein denaturation (range: 10–25%). Consequently, the amount of substrate and the amount of LF to be used in the immobilization reaction will depend, inter alia, on the choice of starting materials. The immobilization technique and the amounts of substrate and LF are readily determined by a skilled artisan without undue experimentation.

Immobilization neutralizes the cationic effect of LF peptide fragments, and eliminates the undesirable, non-specific cidal activity characteristic of lactoferricin. Without intending to be limited by a theory of operation, it is believed that immobilization gives structural stability and bio-functional specificity to the LF protein. This property facilitates the retention and carry-through of Im-LF, even, for example, when Im-LF is applied during an early stage of meat or other food processing.

In preferred embodiments of the inventive compositions and methods, the Im-LF is combined in a mixture with native LF. The molar ratio of immobilized versus native LF in such a mixture is important in providing broad-spectrum activity, and molecular stability of both the immobilized and the native LF. Mixtures of Im-LF and native LF in a ratio of from about 0.25:1 to about 1:10, preferably from about 1:1 to about 1:5, most preferably 1:1 ratio have been found to provide the greatest microbial blocking activity. In one preferred embodiment, the composition is an aqueous solution containing such a mixture of Im-LF and native LF. In some preferred embodiments, the composition contains a mixture of about 1% wt/vol Im-LF and about 1% wt/vol native lactoferrin.

Mixtures of Im-LF and native LF are formed by adding excess LF to the substrate. In a preferred aqueous dispersion embodiment, from about 0.001% wt/vol to about 2.5% wt/vol, preferably from about 0.5% wt/vol to about 2.0% wt/vol, most preferably about 1% wt/vol of LF is added to a dispersion containing 0.01% wt/vol galactose-rich polysaccharide or other substrate as described herein above.

If no native LF is present in the inventive composition (meaning that 100% of the LF is Im-LF), the apparent binding affinity of the Im-LF with a product (e.g., meat) or other biological surface will be lower than the apparent binding affinity of LF or a mixture of Im-LF and LF, thus, yielding relatively lesser retention of Im-LF on the surface over time after the composition is sprayed or otherwise applied. On the other hand, Im-LF, without added native LF, yields enhanced antimicrobial activity compared to LF or a mixture of Im-LF and LF. Thus, a mixture of Im-LF and native LF yields a comparatively higher apparent binding affinity and retention, but if too much native LF is added to the mixture, undesirable non-specific antimicrobial properties will become significant.

Typically, the case-ready food products such as ready-to-eat food products, are treated with a comestible dispersion containing the Im-LF. Suitable dispersions include an aqueous solution, an aqueous emulsion, a colloid, a suspension, a powder, or a granular solid that contains the Im-LF. A "defined dispersion" is a dispersion made, blended, concocted, constructed, synthesized, or assembled of preselected ingredients or components, each in preselected amounts. Dispersion can be accomplished in various ways. A first way is that of a solution, most preferably an aqueous solution containing the Im-LF. In embodiments, in which LF is immobilized on a lipid substrate, such as a triglyceride compound, the lipid can be held in solution if the solution has the properties of bile (i.e., solution of mixed micelles with bile salt added), or the solution has the properties of a detergent or a solvent (e.g., a solution of Tween). A second way is that of an emulsion, i.e., a 2-phase system in which one liquid is dispersed in the form of small globules throughout another liquid that is immiscible with the first liquid. (Swinyard and Lowenthal, "Pharmaceutical Necessities" *REMINGTON'S PHARAMCEUTICAL SCIENCES,* 17th ed., AR Gennaro (Ed), Philadelphia College of Pharmacy and Science, 1985 p. 1296). Aqueous emulsions containing a second hydrophobic liquid phase are preferred. A third way is that of a suspension of a solid phase containing the Im-LF, either dispersed within a liquid phase, such as a colloid suspension of Im-LF, or dispersed among other solids (e.g., microcrystalline suspension), the composition thus having the form of a powder or a granular solid. In various embodiments, such solid dispersions containing Im-LF can be applied to surfaces directly, for example by spraying or can be contained in pharmaceuticals such as tablets, capsules, ointments, or the like. Solid dispersions have obvious advantages with respect to storage and transport, and such solid dispersions containing Im-LF can later be suspended or dissolved in a liquid phase before use, as appropriate or convenient. Any of the solutions, emulsions or suspensions can be incorporated into capsules, or a microsphere or particle (coated or not) contained in a capsule.

In non-liquid dispersion embodiments (e.g., solid dispersions such as powders and granular dispersions), from about 0.001% wt Im-LF/total wt to about 2.5% wt Im-LF/total wt, preferably from about 0.5% wt Im-LF/total wt to about 2.0% wt Im-LF/total wt, most preferably about 1% wt Im-LF/total wt is added to a dispersion containing 0.01% wt Im-LF/total wt galactose-rich polysaccharide or other substrate as described herein above. Similar concentrations of native LF can be added to the non-liquid dispersion embodiments to form mixtures of Im-LF and native LF.

In some embodiments, the comestible dispersion can also include a suitable medium or carrier for convenient mixing or dissolving into a particular food product or for applying to the surface of the food product. Also, in some embodiments, the dispersion additionally contains a mixture of native LF and Im-LF. In such embodiments, the concentration of Im-LF/native-LF mixture in comestible formulations is typically from about 0.001% to 2.5% wt/vol, preferably about 0.5% to 2.0% wt/vol, most preferably about 1% wt/vol.

The dispersion is preferably one that will not interfere with the familiar flavor of the food of interest, such as are known by the artisan skilled in food processing techniques. For example, a comestible aqueous dispersion typically contains water. Suitable emulsifiers include mono-, di-, or triglyceride compounds, glycerol, phosphatidyl ethanolamine, phosphatidyl choline, or lecithin. A most preferred embodiment includes a mixture of mono- and diglyceride compounds, such as found in a commercially available mixture like GRUENAU Mono & Diglycerides, or C.G. 340-E (Bavaria Corporation, Altamonte Springs, Fla.), containing 35–45% monoglycerides.

Optionally, the aqueous dispersion contains other components as are known in the art for preserving or enhancing food products, particularly for meat products, such as brines, starches (e.g., potato starch, corn starch, tapioca starch, or rice starch), maltodextrin, plasma or meat stock proteins, amino acids, protein or starch hydrolysates, antioxidants and/or flavorants. (E.g., C. L. Gilchrist, Method of processing meat, U.S. Pat. No. 5,714,188; P. A. Inklaar, Method of improving dehydrated raw animal meat, U.S. Pat. No. 3,681,095 and Method for improving the quality of meat-containing foods, U.S. Pat. No. 3,552,978; K. Nishimori and Y. Nakao, Method and composition for preventing discoloration of meat products, U.S. Pat. No. 4,590,079; J. H. Ernster, Hydrolyzed protein composition and process used in preparation thereof, U.S. Pat. No. 4,545,933; K. Tamaki et al., Low calorie meat products and a process for producing the products, U.S. Pat. No. 5,039,539).

A flavorant can be a natural extractive of a spice plant or herb, for example, rosemary, sage, basil, oregano or any other pleasant herbal or fruity flavorants or mixture of flavorants. Synthetic flavorants are also suitable. The flavorant can also have antimicrobial properties.

Typically, the concentration of Im-LF on a biological or product surface treated in accordance with the inventive methods is from about 0.0001 to about 10 mg/sq. inch.

In a preferred embodiment, the composition contains a buffer system including a combination of a physiologically acceptable acid, such as oxalic acid, ethylenediamine tetraacetic acid, carbonic acid (which can be added in aqueous form or by gassing an aqueous solution or emulsion with carbon dioxide), or citric acid, preferably ethylenediamine tetraacetic acid and citric acid; a physiologically acceptable base, preferably sodium bicarbonate potassium bicarbonate, sodium carbonate, or potassium carbonate; and a physiologically acceptable salt such as calcium chloride, potassium chloride or sodium chloride, preferably sodium chloride. The citrate and bicarbonate ratio in the buffer is significant for co-ordinated metal binding properties of LF, which play an important factor in enhancing the stasis effect and microbial blocking activity of the LF. The molar ranges of acid:base:salt is typically about 0.1 to 0.0001M (acid): 1 to 0.001M (base): 10 to 0.01M (salt); with 0.01–0.001M (acid): 0.1 to 0.01M (base): 1 to 0.1M(salt), preferred; and 0.001M (acid): 0.01M (base): 0.1M(salt), most preferred. Examples of preferred embodiments are thusly buffered aqueous solutions, emulsions, colloids, or suspensions.

The preferred pH range for aqueous solutions containing Im-LF is about pH 4 to about pH 8, most preferably between about pH 5.5 to about pH 7.5. If a specific pH is desired for a specific application, then to acidify aqueous solutions, any food or pharmaceutical grade acid is employed (e.g., citric, lactic, phosphoric, or acetic acid), as appropriate. To make the dispersion more alkaline, a mono-, di-, or tri-basic phosphate salt is typically used.

A 2% aqueous solution containing Im-LF can be obtained by first preparing a dry blend of 20 g lactoferrin (DMV International Nutritionals, the Netherlands), 0.2 g pectin (CU 201, Herbstreith and Fox, Neuenberg, Germany), 5.8 g sodium chloride (Fisher Scientific, Pittsburgh, Pa.), 0.84 g sodium bicarbonate (Fisher Scientific) and 0.3722 g ethylenediamine tetraacetic acid (Version Na, Dow Chemical, Midland Mich.). Dissolution of the dry blend in 1 liter of water produces a 2% solution.

Similarly an 1% aqueous solution containing Im-LF can be obtained by first preparing a dry blend of 10 g lactoferrin (DMV International Nutritionals, the Netherlands), 0.1 g pectin (CU 201, Herbstreith and Fox Neuenberg, Germany), 5.8 g sodium chloride (Fisher Scientific, Pittsburgh, Pa.), 0.84 g sodium bicarbonate (Fisher Scientific) and 0.3722 g ethylenediamine tetraacetic acid (Versene Na, Dow Chemical, Midland Mich.). Dissolution of the dry blend in 1 liter of water produces an 1% solution.

For sterilizing the Im-LF-containing dispersions, for example aqueous solutions containing Im-LF, aseptic filtration is most preferred, but gamma irradiation is also useful. The Im-LF-containing dispersions are not autoclavable. However they can be pasteurized, which is useful, for example, in many food processing applications.

The inventive methods described herein are useful against a wide variety of bacteria, such as, but not limited to pathogenic and non-pathogenic strains of:

(A) Gram-negative facultative anaerobes of the enteric group, for example, *E. coli; Helicobacter pylori; Salmonella* spp., including *Salmonella typhimurium, Salmonella typhi, Salmonella enteritidis Salmonella abony, Salmonella dublin, Salmonella hartford, Salmonella kentucky, Salmonella panama, Salmonella pullorum, Salmonella rostock, Salmonella thompson, Salmonella virschow; Enterobacter* spp., such as *Enterobacter aerogenes; Klebsiella pneumoniae; Shigella* spp., such as *Shigella dysenteriae* or *Shigella flexneri; Vibrio* spp., including *Vibrio cholerae; Yersinia enterocolitica* and *Yersinia pestis.*

(B) Gram-negative aerobic motile rods such as *Bordetella pertussis; Campylobacter jejuni*; and *Pseudomonas* spp., such as *Pseudomonas aeruginosa;*

(C) Gram-negative aerobic non-motile rods such as *Brucella* spp. *Legionella pneumophila*; and *Francisella tularensis;*

(D) Gram-positive bacteria, including coccoid forms such as *Listeria monocytogenes, Staphylococcus* spp., such as *Staphylococcus aureus, Staphylococcus epidermidis; Streptococcus* spp., such as, *Streptococcus pyogenes, Streptococcus pneumoniae, Streptococcus mutans, Streptococccus sanguis; Pediococcus acne*; and bacillary forms such as *Bacillus* spp., including *Bacillus cereus, Bacillus anthracis, Bacillus pumilus, Bacillus subtilis; Clostridium* spp., including *Clostridium difficile, Clostridium tetani, Clostridium botulinum*, and *Clostridium perfringens.*

The inventive methods can, optionally, be used in combination with other known antimicrobial agents, including lacto-antimicrobials, such as lactoperoxidase, lactoglobulins, lactooligosaccharides, lactolipids, lactoglobulins; ovo-antimicrobials, such as ovotransferrin, lysozyme, avidin, ovoglobulin, riboflavin-binding protein, ovomucoid protease inhibitor; phyto-antimicrobials, such as thiosulfinates, glucosinolates, flavonoids, essential oils, phenolates, catechins; bacteriocins, such as nisin, pediocin, reuterin, or sakacin; acid-antimicrobials, such as lactic acid, acetic acid, citric acid, sorbic acids; ionic antimicrobials, such as polyphosphates, nitrites; sulfur-compounds; chlorocides; ozone; or a natural, synthetic, or an semi-synthetic antibiotic agent, such as neomycin, metronidazole, teicoplanin, vancomycin, ciprofloxacin, doxycycline, tetracycline, augmentin, erythromycin, chloramphenicol, cephalexin (e.g., Keflex), penicillin, ampicillin, kanamycin, rifamycin, rifaximin, rifampin, clindamycin, trimethoprim, a 4-amino salicylate compound, a 5-aminosalicylate compound, a sulfonamide compound, a betalactam compound, an aminoglycoside compound, a macrolide compound, a quinolone compound, acidified sodium chlorite, Inspexx-100, or cetylpyridinium chloride (CPC).

Moreover, the Im-LF-containing compositions can act synergistically to potentiate some antibiotic agents, including beta-lactams, chloramphenicol, aminoglycosides, clindamycin, vancomycin, sulfonamides, trimethoprim, rifampin, tetracyclines, metronidazole, quinolones, erythromycin and other macrolides.

The inventive methods are especially effective in treating food-borne pathogens, food-borne radiation-resistant bacteria, and other food spoilage microorganisms, including fungi, viruses and parasites. For example, the inventive methods described herein are of use in preventing, reducing, and/or inhibiting microbial growth or contamination by a wide variety of bacteria, including enterotoxigenic *E. coli*, enteropathogenic *E. coli, Shigella* spp., including *Shigella dysenteriae, Shigella flexneri, Salmonella* spp., including *Salmonella typhimurium, Salmonella abony, Salmonella dublin, Salmonella hartford, Salmonella kentucky, Salmonella panama, Salmonella pullorum, Salmonella rostock, Salmonella thompson, Salmonella virschow, Listeria* spp., including *Listeria monocytogenes, Campylobacter* spp, including *Campylobacter jejuni, Aeromonas hydrophila, Staphyloccus* spp., including *Staphylococcus aureus, Staphylococcus hyicus, Staphylococcus epidermidis, Staphylococcus hominis, Staphylococcus warneri, Staphylococcus xylosus, Staphylococcus chromogenes Bacillus* spp., including *Bacillus cereus, Bacillus subtilis, Candida albicans, Hafnia* spp., *Aeromonas* spp., *Bacillus* spp., *Citrobacter* spp., *Klebsiella* spp., *Micrococcus* spp., *Achromobacter* spp., *Proteus* spp. and such radiation-resistant bacteria as: *Brochothrix* spp., including *Brochothrix thermospacta, Bacillus pumilus, Arcobacter* spp., including *Arcobacter butzleri, Enterococcus* spp., including *Enterococcus faecium, Pseudomonas* spp., including *Pseudomonas fluorescencel, Shewanella* spp., including *Shewanella putrefaciens, Enterobacter* spp, including *Enterbacter cloa, Deinococcus* spp., including *Deinococcus radiopugnans, Deinococcus radiodurans, Deinobacter grandis, Flavobacterium* spp., including *Flavobacterium aquatile, Acinetobacter* spp., including *Acinetobacter baumannii, Acinetobacter calcoaceticus*, and *Acinetobacter radioresistens, Methylobacterium radiotolerans*, as well as other kinds of bacteria described herein above. In particular, microbial contamination by verotoxic *E. coli,* including serotype O157:H7 and *Listeria monocytogenes* can be prevented by the inventive technology. In addition, the inventive methods described herein are of use in preventing, reducing, and/or inhibiting microbial growth or contamination by a wide variety of food spoilage fungi, including *Cladosporium* spp., *Mucor* spp., *Rhizopus* spp., *Penicillum* spp., *Geotrichium* spp., *Sporotrichium* spp., *Candida* spp., *Torula* spp., and *Rhodotorula* spp.

Any foodstuff can be treated using the inventive method, but foods for which the present method is especially useful include non-acidic foods, such as mayonnaise or other egg products, potato products, and other vegetable or meat products, as well as combinations of such products. Representative products include processed and unprocessed foodstuffs for human or for animal consumption.

For example, foodstuffs or food products include any suitable meat or meat product derived from, but not limited to, pork, beef, veal, lamb, sheep, goat, bison, elk, deer, antelope, horse, dog, poultry (e.g., such as chicken, turkey, duck, goose, guinea fowl, ostrich, quail, dove, pigeon, emu, pea hen), or the meat of any other mammalian or bird (avian) species. A “beef product” contains the meat of an adult mammal of the subfamily Bovinae, including cattle, buffalo, bison, and kudus. A “pork product” contains the meat of a pig. A “poultry product” contains the meat of a bird, such as a chicken, duck, goose, turkey, ostrich, emu, dove, pigeon, quail, pheasant, peafowl, or guinea fowl. “Meat” includes whole or ground muscle or organ (e.g. liver).

The meat products that can be treated in accordance with the invention include, but are not limited to, primal, subprimal, or case-ready products, such as ready-to-eat meat products including, sliced cuts of meat, with or without bone, and ground meat. Primals are the initial divisions of the animal carcass after slaughter, for example, major wholesale cuts such as the shoulder, belly, loin, ham, or bone-in-loin. Subprimals are subdivisions of primal cuts, such as tender loins or back ribs. Case-ready meat products including ready-to-eat meat products, are smaller subdivisions of subprimal cuts, such as chops, steaks, or ground meat products, such as sausages, salamis, bologna, pepperonis, frankfurters, hotdogs and the like, or cold cuts, such as processed deli meats, including cured meats, ham, turkey, and the like. Representative ready-to-eat products include cold beef, turkey and ham, ethnic meat products, such as sushi-grade meats, Korean marinated meats, Mexican marinated meats, chicken, turkey and ham salads, and the like. Ready-to-eat poultry products include cooked and/or roasted whole chicken, nuggets, wings, breast strips, thighs, drumsticks, and the like. The inventive method is also useful in treating ready-to-eat breakfast, lunch and dinner products including frozen foods that may contain vegetables, dairy ingredients, sauces, broths, gravies, and the like.

The food product is typically a packaged meat product treated in accordance with the present method. Packaging may be by any conventional meat packaging means, including containing the meat product with a tray, a transparent film, such as shrink-wrap or Saran, vacuum packaging, or packaging with a paper, including unwaxed or waxed paper, or wrapping, bagging, boxing, canning or jarring by any means suitable for a meat product.

Foodstuffs and food products also include the surfaces and/or flesh of marine or freshwater aquatic organisms, such as various fishes (e.g., tuna, salmon, halibut, cod, shark, swordfish, bass, herring, sardines, trout, carp, whitefish, and perch), mollusks (clams, scallops, oysters, mussels, snails, octopus, and squid), or crustaceans (e.g., crabs, shrimps, lobsters, and crayfish). Surfaces can include surfaces of edible parts or exposed inedible parts that are subject to contamination, such as shells, cuttlebones, or carapaces. Also included among foodstuffs or food products are vegetable foodstuffs and food products, which can include any edible fruits, seeds, nuts, roots, tubers, bulbs, stems, leaves, flower parts, blades, stipes, holdfasts, or sporangia of terrestrial or aquatic plants or algae.

The Im-LF-containing composition is applied by any suitable method. Representative methods include spraying the product or washing the product during various processing steps, or coating the final product by electrostatic spray dispersion, with an aqueous suspension, emulsion, or solution, or dehydrated powder form containing the Im-LF.

The Im-LF-containing composition is applied at any time during the preparation of the product to be treated. For example, when the product is a meat, the Im-LF can be applied during slaughter or during the carcass wash or, if the meat product is a ground meat product, during meat grinding or homogenization. After application, the concentration of Im-LF on the food surface typically ranges from 0.0001 to 10 mg/sq. inch of food surface, more preferably 0.01 to 1 mg/sq. inch of food surface, most preferably 0.25 mg/sq. inch of food surface.

For treating meat products or other foodstuffs that are preferably stored and transported at refrigerated temperatures, the components of an aqueous dispersion, preferably in the form of a solution or emulsion, are mixed, then the dispersion is chilled, preferably to 32–36 EF, most preferably to 32–33EF, before applying it to the foodstuff. The chilled dispersion is applied to the meat or other foodstuff.

The aqueous dispersion can be applied externally to the meat or other foodstuff to form a coating on its surface by spraying, brushing, or soaking it with the solution or emulsion.

Alternatively, in some embodiments of the inventive meat product, the aqueous dispersion is applied internally so that it penetrates the surface of the flesh and/or bone. One way this is accomplished is by injecting the solution into the meat. Alternatively, the meat is soaked in the solution for a period ranging from two hours up to two days. This provides lesser penetration of solution than injection. However, by massaging or tumbling the meat while it is being soaked, greater penetration of solution is achieved, and shorter soaking times are required, for example 30 to 60 minutes. The degree of penetration by the solution depends on the speed (rpm) of massaging or tumbling that is employed, soak time, the specific formulation of the aqueous solution, and whether vacuum is applied during massaging or tumbling. Typically, good results are obtained using 30 minutes of massaging or tumbling with an applied vacuum, followed by release of vacuum, and then a second 30 minute period of tumbling with vacuum.

In some embodiments of the present invention, an Im-LF-containing coating is applied as a fine spray to form a film on the interior surface of casings before the casings are stuffed with a batter for making sausages, salamis, hot dogs or the like. For example, a suitable coating formulation is made by combining 1% Im-LF immobilized on GRP combined with a film-forming agent such as carrageenan, gelatin or collagen (type-I and type-II). The microbial blocking activity is retained and works to prevent microbial contamination of the encased food product.

The treatment with Im-LF can be used either used singularly or in combination with other microbiological decontamination interventions. Other suitable microbiological decontamination interventions include treatment of the food products with ozone or by thermal pasteurization or non-thermal decontamination including high pressure processing, electrolyzed oxidizing water, ionizing radiation including E-beam, and the like. When more than one intervention is employed, generally, they can be employed in any sequence.

After treatment in accordance with the present method, the treated meat product or other foodstuff is optionally packaged, for example, vacuum packaged. Regardless of packaging, the treated meat product is most preferably stored under refrigerated conditions until final purchase by the consumer. A meat product is typically stored at a temperature between 29–40EF, preferably between 29–38EF, and most preferably at 29–34EF. Alternatively, the treated meat product is stored frozen.

Optionally, the packaged meat product can be stored and transported to market under a controlled gas mixture to preserve product color or other consumer desirability factors, as is known in the art. (E.g., C. S. Cheng, Process for prepacking fresh meat, U.S. Pat. No. 4,683,139; Hormel Foods Corporation, Chemical treatment and packaging process to improve the appearance and shelf life of fresh pork, U.S. Pat. No. 5,780,085).

The Im-LF in accordance with the invention is also useful in coatings or meat packaging materials. In some embodiments, 2% Im-LF is applied to wax-coated wrappings, cellulosic or polyethylene liners used as packing materials in meat industry. The coating is stable with full retention of its microbial blocking activity.

This method also is intended for bacteriostatic food packaging or handling and relies on the antimicrobial properties of Im-LF, in accordance with the present invention. The present method involves treating a food-contacting surface of a material that is pharmaceutically acceptable for food packaging or food handling purposes, with an Im-LF in an amount effective to inhibit the growth of a microbial species on a food contacting the surface.

Acceptable materials for food packaging or handling, in accordance with the invention, include, but are not limited to, paper, wood, cardboard, or other cellulosic polymers, including transparent and non-transparent cellulosic polymers, to which LF can be attached by its N-terminal moiety.

A food-contacting surface of a suitable polymeric material is treated with lactoferrin by enmeshing, implanting, or impregnating the compound within the polymeric material, by means known to the artisan skilled in food packaging and handling materials. The treated food-contacting surface has an amount of Im-LF between about 0.0001 to about 10 mg/square inch of food-contacting surface, more preferably about 0.01 to about 1 mg/sq. inch. This is sufficient concentration to inhibit the growth of a food-poisoning or botulism-causing bacterial species.

Alternatively, a suitable polymeric material is treated with Im-LF by covalent linkage, such as by conjugation of the Im-LF to the polymeric material through, for example, diazo bonds or amide bonds.

Alternatively, a polymeric or non-polymeric material is treated with Im-LF by coating the material with a coating formulation suitable for a desired coating means, such as, but not limited to, dipping, spraying or brushing onto a surface intended for food contact. A suitable coating formulation contains, in addition to Im-LF, an appropriate carrier (s), which carriers are known in the art. For example, the skilled practitioner can employ as a carrier a non-toxic polymeric resin, additionally containing an effective amount of Im-LF, which resin can be used to coat the food-contacting surface of the material, hardening in place upon it.

Direct sampling is conventionally used to measure bacterial numbers foodstuffs, including meat and meat products. Samples can be macerated and diluted and bacterial numbers can be assessed by conventional microbiological means such as, but not limited to colony plating or Most Probable Number (MPN) techniques, or direct counting of bacterial cells. For direct bacterial cell counts, cells can optionally be labeled with specific markers, and counts can be accomplished manually or by well-known devices such as fluorescence-activated cell sorting (FACS).

A hygienic condition is maintained in accordance with the present invention through the inhibition of microbial growth on meat products and other foodstuffs treated thereby, based on a suitable hygienic standard as defined in the art.

The present invention is also related to food containers and food-handling implements for holding a foodstuff, which includes containing, packaging, covering, storing, displaying, processing, cutting, chopping, impaling, kneading, manipulating or otherwise handling the foodstuff, such that a surface of the food container or implement comes in contact with the foodstuff.

The present food containers and food-handling implements comprise a material suitable for contact with food and have a food-contacting surface treated with Im-LF, as described above, in an amount effective to inhibit the growth and/or adhesion of a bacterial or other microbial species thereon. An effective amount is between about 0.0001 to about 10 mg/square inch of said food-contacting surface, more preferably about 0.01 to about 1 mg/sq. inch. The containers and implements are in any suitable disposable (i.e., single-use) or non-disposable (i.e., multi-use) configuration capable of holding a foodstuff. These configurations include, but are not limited to, shear wraps, sheets, papers, waxed papers, bags, cartons, trays, plates, bowls, covered and uncovered storage vessels, serving dishes, cups, cans, jars, bottles, or any other suitable container configuration for a particular foodstuff. Additional configurations especially useful for food handling purposes include, but are not limited to, gloves or mitts; utensils such as forks, spoons, knives, slicers, processors, juicers, grinders, chippers, hooks, presses, screws, belts, openers, cutters, peelers, tongs, ladles, scoops, cups, chutes or spatulas; and cutting boards, kneading boards, mixing bowls, drying or cooling racks, or shelves.

The inventive containers, and implements are especially useful in inhibiting the growth and/or adhesion of food-poisoning bacterial species, such as enterotoxigenic *Escherichia coli, Salmonella* spp., or *Shigella* spp., or species that can release pathogenic exotoxins, such as, but not limited to, *Clostridium perfringens*, or *Clostridium botulinum*, the exotoxins of which cause botulism. They are especially, but not exclusively, useful in commercial and institutional food preparation contexts where food is handled and packaged in bulk, such as, but not limited to, food processing factories, canning plants, slaughterhouses, restaurants, cafeterias, salad bars, grocery outlets, and hospitals. The present method, containers and implements are useful for any kinds of foodstuff. They are particularly useful in situations where food is processed, packaged, stored, or displayed at a temperature, at or above room temperature, but insufficiently hot to kill bacterial cells and spores, for example, when food is kept under a warming light. But the present method, containers and implements are also useful in the home kitchen.

I claim and desire to protect by Letters Patent:

1. A case-ready food product containing isolated lactoferrin immobilized on a naturally occurring substrate via the N-terminus region of the lactoferrin in a concentration between about 0.0001 and about 10 mg per gram of the food product.

2. The case-ready food product in accordance with claim 1 wherein the food product is a meat product.

3. The case-ready food product in accordance with claim 2 wherein the meat product is a beef product, a pork product, or a poultry product.

4. The case-ready food product in accordance with claim 2 wherein the concentration of lactoferrin on the surface of the meat product is from about 0.01 to about 1 mg/sq. inch.

* * * * *